United States Patent [19]

Giesecke et al.

[11] Patent Number: 4,467,099

[45] Date of Patent: Aug. 21, 1984

[54] GLYCIDYL-1,2,4-TRIAZOLIDINE-3,5-DIONES

[75] Inventors: Henning Giesecke, Cologne; Rudolf Merten, Leverkusen; Ludwig Rottmaier, Odenthal, all of Fed. Rep. of Germany

[73] Assignee: Bayer Aktiengesellschaft, Leverkusen, Fed. Rep. of Germany

[21] Appl. No.: 278,646

[22] Filed: Jun. 29, 1981

[30] Foreign Application Priority Data

Jul. 21, 1980 [DE] Fed. Rep. of Germany ....... 3027623

[51] Int. Cl.³ .......................................... C07D 405/14
[52] U.S. Cl. ...................................... 548/264; 8/115.6; 428/414; 428/415; 428/417; 428/418
[58] Field of Search ........................................ 548/264

[56] References Cited

U.S. PATENT DOCUMENTS 3,634,445  1/1972  Zschocke et al. ............... 260/308 C
3,681,374  8/1972  Yano et al. ....................... 260/308 R
4,283,546  8/1981  Rottmaier et al. .................. 548/264

OTHER PUBLICATIONS

Chemical Abstracts, vol. 61, No. 3, 3094–3095, Abstract No. 3094h, 3/8/64.

Primary Examiner—Alton D. Rollins
Attorney, Agent, or Firm—Connolly and Hutz

[57] ABSTRACT

Glycidyl-1,2,4-triazolidine-3,5-diones corresponding to the general formula I

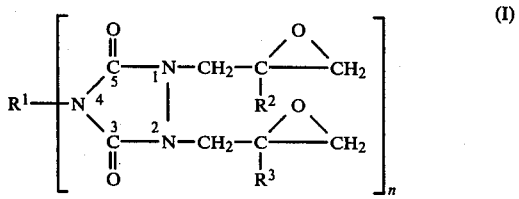

wherein $R^1$ represents a mono- to pentavalent substituted or unsubstituted straight-chain or branched-chain $C_1$–$C_{30}$ aliphatic group, a mono- to pentavalent substituted or unsubstituted $C_5$–$C_{21}$ cycloaliphatic group, a mono- to pentavalent substituted $C_7$–$C_{17}$ aliphatic-aromatic group or a mono- to pentavalent substituted or unsubstituted $C_6$–$C_{21}$ aromatic group, the above mentioned aliphatic group being optionally interrupted by one or more oxygen atoms or tertiary nitrogen atoms, and the above mentioned aliphatic-aromatic, polynuclear and cycloaliphatic polynuclear aromatic groups being optionally interrupted by at least one oxygen or tertiary nitrogen atom or by at least one $C_1$–$C_4$ alkylene group or by at least one sulphonyl group

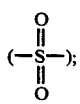

$R^2$ and $R^3$, which may be identical or different, each represents a hydrogen atom or a methyl group, and n represents a number from 1 to 5.

8 Claims, No Drawings

GLYCIDYL-1,2,4-TRIAZOLIDINE-3,5-DIONES

This invention relates to new glycidyl-1,2,4-triazolidine-3,5-diones of the general formula (I)

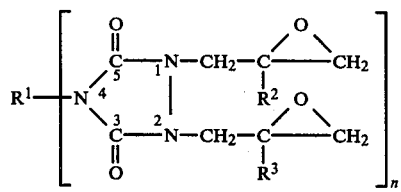

wherein $R^1$ represents a monovalent to pentavalent substituted or unsubstituted straight-chain or branched-chain aliphatic $C_1$–$C_{30}$, preferably $C_1$–$C_{12}$ group, a monovalent to pentavalent substituted or unsubstituted cycloaliphatic $C_5$–$C_{21}$ group, a monovalent to pentavalent substituted or unsubstituted aliphatic-aromatic $C_7$–$C_{17}$, preferably $C_7$–$C_{10}$ group, or a monovalent to pentavalent substituted aromatic $C_6$–$C_{21}$, preferably $C_6$–$C_{15}$ group, the above mentioned aliphatic groups being optionally interrupted by one or more oxygen atoms or tertiary nitrogen atoms, and the above mentioned polynuclear aliphatic-aromatic, polynuclear cycloaliphatic and polynuclear aromatic groups being optionally interrupted by at least one oxygen atom or tertiary nitrogen atom or by at least one alkylene group having 1 to 4 C-atoms or by at least one sulphonyl group

$R^2$ and $R^3$ are identical or different and each represents a hydrogen atom or a methyl group, preferably a hydrogen atom, and n represents a number from 1 to 5, preferably 1 to 3.

The substituents on $R^1$ are preferably the following:

Alkoxycarbonyl groups preferably having 1 to 4 C-atoms in the alkoxy moiety, CN, $NO_2$, alkylmercapto groups having 1 to 4 C-atoms in the alkyl group, dialkylamino groups preferably having 1 to 6 C-atoms in each alkyl group, halogen atoms, (preferably fluorine, chlorine or bromine) and in the case of aromatic groups also lower alkyl groups with preferably 1 to 4 C-atoms in addition to the above mentioned substituents.

Compounds of formula (I) in which $R^1$ is unsubstituted and $R^2$ and $R^3$ are hydrogen are particularly preferred.

The following formulae represent examples of preferred groups $R^1$:

(a) $C_xH_{2x+1}$—  $x = 1$ to 18
(b) —$(CH_2)_m$—  $m = 2$ to 12

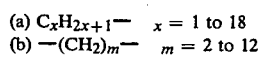
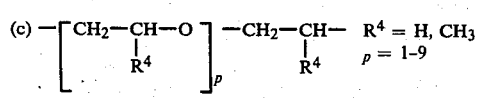

-continued

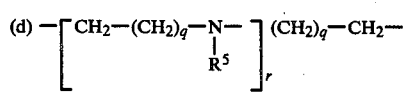

$R^5 = C_1$–$C_4$—alkyl
$q = 1$–2
$r = 1$–4

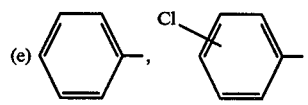

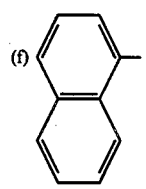

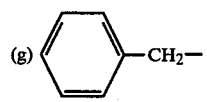

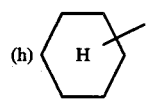

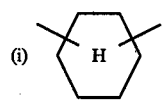

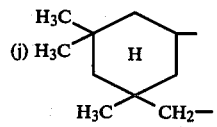

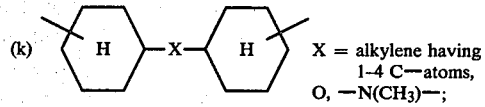

X = alkylene having 1–4 C—atoms, O, —N(CH$_3$)—;

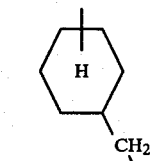

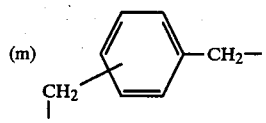

-continued

  (n)

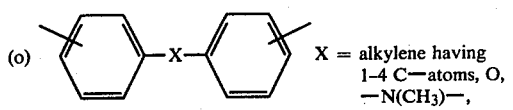  (o)  X = alkylene having 1-4 C—atoms, O, —N(CH$_3$)—,

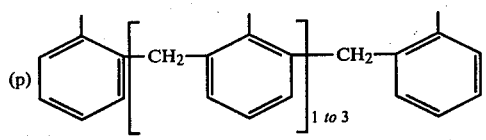  (p)

(q) C$_4$H$_9$—O—CH$_2$—CH$_2$—CH$_2$—

(r) —(CH$_2$)$_3$—O—(CH$_2$)$_{2\ to\ 4}$O—(CH$_2$)$_3$—

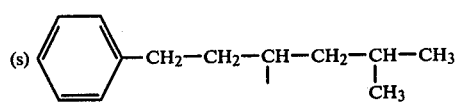  (s)

The triazolidine-3,5-diones required as starting materials for the preparation of the glycidyl-1,2,4-triazolidine-3,5-diones of formula (I) according to the invention may be obtained by various methods.

For example, amines of formula (II)

$$R^1(NH_2)_n \quad (II)$$

wherein $R^1$ and n have the meanings indicated in formula I, may be reacted with hydrazodicarbonamide (Method 1) or with 1,2,4-triazolidine-3,5-dione (Method 2) at 150° C. to 280° C. either in the presence or absence of a solvent such as N-methylpyrrolidone or a solvent mixture at pressures of from 50 mbar to 5 bar, optionally in the presence of an acid or basic catalyst such as alcoholates or tertiary amines, so that ammonia is split off and 1,2,4-triazolidine-3,5-diones are obtained as starting materials.

Another method of preparing the 1,2,4-triazolidine-3,5-diones used as starting materials comprises reacting N-monosubstituted hydrazodicarbonamides of formula (III)

$$[H_2N—CO—NH—NH—CO—NH—]_nR^1 \quad (III)$$

wherein $R^1$ and n have the meanings indicated in formula I, under the conditions indicated above for Methods 1 and 2 to form the desired 1,2,4-triazolidine-3,5-diones with liberation of ammonia. N-Mono-substituted hydrazodicarbonamides of formula (III) may be obtained by known methods from semicarbazide and iscoyanates of formula (IV)

$$R^1(NCO)_n \quad (IV)$$

wherein $R^1$ and n have the meanings indicated in formula I.

The glycidyl-1,2,4-triazolidine-3,5-diones according to the invention corresponding to the general formula(I) are obtained by reacting 1,2,4-triazolidine-3,5-diones of formula (V):

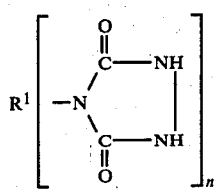  (V)

wherein $R^1$ and n have the meanings indicated in formula I, with an epihalohydrin or β-methylhalohydrin, e.g. with epichlorohydrin, epibromohydrin or β-methylepichlorohydrin in known manner, optionally in the presence of a suitable catalyst, or with 1,3-dihalohydrinpropane in the presence of a hydrogen halide liberating agent, followed by treatment with hydrogen halide acceptors to liberate the hydrogen halide. The process of preparation of the glycidyl-triazolidine-3,5-diones of formula (I) may also be carried out in a single stage by reacting 1,2,4-triazolidine-3,5-diones of formula (V) with an epihalohydrin or 1,3-dihalohydrinpropane in the presence of hydrogen halide liberating agents such as sodium or potassium hydroxide.

In the preferred two-stage process, 1,2,4-triazolidine-3,5-diones of formula (V) are reacted with an epihalohydrin in a first stage, in the presence of basic, acid or neutral catalysts, to form the halohydrin compound corresponding to the general formula (VI):

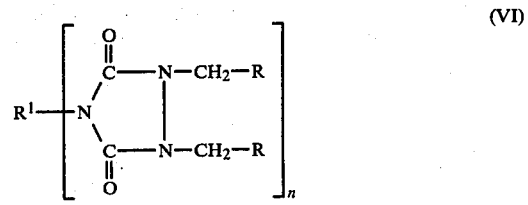  (VI)

in which the groups R are capable of conversion into 1,2-epoxyethyl groups. In the formula, $R^1$ and n have the meanings indicated in formula I.

Suitable groups R, which are capable of conversion into a 1,2-epoxyethyl group, are mainly hydroxyhaloethyl groups which carry functional groups on various carbon atoms, e.g. 2-chloro-1-hydroxy- or 2-methyl-2-chloro-1-hydroxyethyl groups.

For addition of the halohydrin, it is advantageous to use as catalysts, tertiary amines and/or quaternary ammonium salts, such as trimethylbenzylammonium hydroxide, tetraethylammonium chloride trimethylbenzylammonium chloride and trimethylphenylammonium chloride, triethylamine, tri-n-butylamine, triethanolamine, N,N'-dimethylaniline, benzyldimethylamine, pyridine, endoethylenepiperazine and N,N'-dimethylpiperazine.

Commercially available basic iron exchanger resins having tertiary or quaternary amino groups or acid amide groups are also suitable.

Low molecular weight thioethers and/or their sulphonium salts such as diethylsulphide, dibenzylsulphide, β-hydroxyethyl-ethylsulphide, thiodiglycol or dibenzyl-methyl-sulphonium bromide or compounds which can react with epihalohydrin to form thioethers or their sulphonium compounds, e.g. hydrogen sulphide, sodium sulphide or mercaptan, may also be used as catalysts.

Alkali metal and alkaline earth metal salts such as lithium chloride and calcium thiocyanate may also be used.

The quantity of catalyst is preferably from 0.01 to 5 mol-%, based on the quantity of 1,2,4-triazolidine-3,5-dione of formula (V).

The halohydrin compound of general formula (VI) may also be prepared by the reaction of 1,2,4-triazolidine-3,5-dione of formula (V) with a dihalohydrin propane such as 1,3-dichloropropanol-2 or 2-methyl-1,3-dichloropropanol-2 in the presence of hydrogen halide liberating agents such as alkali metal or alkaline earth metal hydroxides, e.g. sodium and barium hydroxide, alkali metal or alkaline earth metal carbonates, e.g. sodium carbonate or calcium carbonate, and tertiary amines such as triethylamine.

The reaction of the 1,2,4-triazolidine-3,5-diones of formula (V) with the epihalohydrin is carried out using at least equivalent quantities of epihalohydrin, i.e. one NH group of the 1,2,4-triazolidine-3,5-diones, of formula (V) is reacted with at least one mol of epihalohydrin. It is preferred, however, to use an excess of epihalohydrin i.e. 1.2 to 20 mol, preferably 3 to 10 mol of epihalohydrin per NH group. The quantity of epihalohydrin will, of course, be kept as low as possible for economical reasons.

The reaction between the 1,2,4-triazolidin-3,5-diones of formula (V) and epihalohydrin is carried out at 20° to 200° C., preferably at 50° to 160° C., optionally under elevated pressure.

The reaction times may generally vary from 30 minutes up to several days and may evan in special cases, be above or below these limits. Shorter reaction times may be obtained by suitable choice of the reaction conditions, e.g. the pressure.

The reaction of 1,2,4-triazolidine-3,5-diones of formula (V) with the epihalohydrin or β-methylhalohydrin may in principle also be carried out without the addition of catalysts although in such cases higher temperatures and/or longer reaction times than those indicated above are then required.

In a second reaction stage, the halohydrin compound, which may already contain certain quantities of glycidyl compounds, depending on the amount of epihalohydrin or β-methylhalohydrin used in excess, is dehydrohalogenated to the glycidyl-1,2,4-triazolidine-3,5-diones of the formula I by means of hydrogen halides liberating compounds.

Compounds which are alkaline in reaction used for liberating hydrogen halides include in particular alkali metal and alkaline earth metal hydroxides such as sodium hydroxide, potassium hydroxide and calcium hydroxide, sodium hydroxide being preferred. This may be used as solids or in solution, preferably in 20 to 50% solutions.

The compounds used for hydrogen halide liberation may also be alkali metal carbomates, in particular sodium carbonate and potassium carbonate in solid form or in solution, or alkali metal silicates, alkali metal phosphates, alkali metal aluminates or excess epihalohydrin or 1,2-alkylene oxides such as ethylene oxide. When epichlorohydrin is used, this is converted into glycerodichlorohydrin.

From 1 to 1.2 equivalents of the hydrogen halide liberating compound is used for each halohydrin group of the 1,2,4-triazolidine-3,5-diones of the formula VI.

In the reaction in which hydrogen halide is liberated, the pH should not exceed 13 and preferably should not rise above 11. To achieve this, the alkali is added gradually or the solution is gradually added dropwise and the pH of the reaction mixture is maintained at the same time.

Liberation of the hydrogen halides may be carried out within the temperature range of 5° to 120° C. If alkalies are used for this purpose, e.g. potassium hydroxide solution, the reaction temperature should not exceed 70° C. if optimum yields are to be obtained. The best results are obtained at temperatures around 30° to 35° C. When using alkali metal carbonates, however, the temperature should rise above 70° C., the maximum temperature being generally determined by the boiling point of the excess epihalohydrin.

In the process of dehydrohalogenation, it is advantageous to add water-immisible organic solvent so that the water formed in the reaction or added dropwise with the alkali solution can be removed azeotropically. The quantities of solvent used are not critical. Chlorinated hydrocarbons such as methylene chloride, chloroform, ethylene chloride and trichloroethylene are suitable solvents. If a large excess of epihalogenhydrin has been used for the formation of the 1,2,4-triazolidin-3,5-dionechlorohydrin compounds of formula VI, the excess epihalohydrin may function as a water-immiscible solvent.

According to a preferred embodiment, 1,2,4-triazolidine-3,5-diones of formula (V) are first reacted with the epihalohydrin, preferably epichlorohydrin, in the presence of a catalyst, preferably a tertiary amine, a quaternary ammonium base, a quaternary ammonium salt or an organic sulphide or sulphonium salt, and the resulting 1,2,4-triazolidine-3,5-dione containing halohydrin groups is then treated in a second stage with hydrogen halide liberating compounds, in particular with alkali metal hydroxides, alkaline earth metal hydroxides or alkali metal carbonates either in solid form or in solution.

The 1,2,4-glycidyl-triazolidine-3,5-diones of formula (I) are generally worked up by suction filtration to remove the by-product of hydrogen halide liberation, e.g. sodium chloride with sodium hydroxide has been used as the acid acceptor. Any residues of sodium chloride and alkalies still present are then removed by washing with water. If desired however, the total quantity of sodium chloride and any residues of alkali may, of course, be removed by washing with water without first carrying out a suction filtration.

The solution remaining behind may now be dried over a suitable dehydrating agent such as anhydrous sodium sulphate. It is then freed from solvent, e.g. excess epichlorohydrin, optionally under vacuum, and the solvent removed may be used for subsequent batches. The pale yellow, viscous oil obtained after removal of the solvent may then be crystallised by dissolving it in suitable solvents such as $C_1$-$C_4$ alkanols, preferably methanol, or ketones such as butanone, glycol monoethers or diglycolmonoethers or their acetates such as ethyleneglycol monomethylether, diethyleneglycol monoethylether and ethyleneglycol monomethylether acetate followed by cooling.

The crystalline compounds obtained may be suction filtered and optionally purified by recrystallisation, e.g. from methanol. In many cases, however, purification may be dispensed with and the crude product used as such for further processing. Depending on the constitutions of the group $R^1$, products in the form of thin liquids to highly viscous resins are frequently obtained, which may be used for further reactions without purification.

The 1,2,4-glycidyl-triazolidine-3,5-diones according to the invention corresponding to formula (I) have epoxide values of 0.2 to 0.91, preferably of 0.64 to 0.91. By "epoxide value" is meant the number of epoxide equivalents contained in 100 g of the substance. The epoxide equivalent is defined as the quantity of substance in grams which contains one 1,2-epoxide group. One 1,2-epoxide group is equivalent to 1 mol of hydrogen halide. The polyglycidyl compounds of the 1,2,4-triazolidine-3,5-diones may still contain some saponifyable halogen (up to ca. 5% by weight of chlorine or ca. 13% by weight of bromine) from their process of preparation. This may, if desired, be removed virtually completely by further treatment with hydrogen halide liberating substances so that the epoxide group content may be in some cases increased.

The compounds according to the invention corresponding to formula (I) may in principle be prepared from compounds of formula VI in which R is a vinyl group ($CH_2=CH-$) by peroxidation, e.g. using hydrogen peroxide or per acids.

The 1,2,4-glycidyl-triazolidine-3,5-diones according to the invention corresponding to formula I, polyglycidyl compounds may be used, either alone or together with the usual hardners, to serve as impregnating agents for textiles, e.g. for polyester fibres, as coatings, e.g. for painting on glass, metal or wood, as adhesives for various polymers products, e.g. for bonding non-woven textile products, and for the production of shaped products such as moulded or pressed bodies and laminates.

In the following Examples, which serve to explain the invention in more detail, the percentages and parts given are based on weight unless otherwise indicated.

EXAMPLES

Preparation of 1,2,4-triazolidine-3,5-diones of Formula (V) used as starting materials.

Starting material 1

600 g of hydrazodicarbonamide and 150 g of ethylene diamine in 500 ml of N-methylpyrrolidone are stirred for 4 hours at 175° C. and then 20 hours at 200° C. The precipitate which forms on cooling is suction-filtered and washed with ethanol. 462 g (80% of the theoretical yield) of 1,2-ethanediyl-4,4'-bis-1,2,4-triazolidine-3,5-dione are obtained as colourless crystals m.p. >330° C.

| | | C | H | N |
|---|---|---|---|---|
| $C_6H_8N_6O_4$ | Calc.: | 31.58 | 3.53 | 36.83 |
| (228.2) | Found: | 31.4 | 3.6 | 36.8 |

IR (KBr): 1731, 1673 cm$^{-1}$ (C=O).

Starting material 2

420 g of 4,4'-diaminodicyclohexylmethane and 472 g of hydrazodicarbonamide in 750 ml of N-methylpyrrolidone are stirred for 4 hours at 175° C., 8 hours at 200° C. and 4 hours at 220° C. The reaction product is cooled and then stirred into 3 l of water. A precipitate forms, which is suction-filtered and washed with water. 566 g (75% of the theoretical yield) of 4,4'-bis-(1,2,4-triazolidine-3,5-dion-4-yl)dicyclohexylmethane are obtained as colourless crystals melting at 305° C. (decomposition). MS (m/e): Mol peak 378.

Starting material 3

Sodium carbonate is added in small portions to a solution of 111.5 g of semicarbazide hydrochloride in 700 g of water until no more evolution of gas is observed.

A solution of 119 g of phenyl isocyanate in 100 g of acetone is then added dropwise at 40° C. Stirring is continued for 2 hours at 40° C. to complete the reaction and the precipitate formed is isolated by suction-filtration.

After it has been left to dry overnight in air, the precipitate is suspended in 300 g of Sulfolan and heated to 205° C. Starting at 160° C., the ammonia liberated is removed by application of a water jet vacuum of 420 mbar. After a reaction time of 5 hours, most of the solvent is removed at a pressure of 0.3 mbar. and the residue is recrystallised from n-butanol. After suction-filtration and drying, 134 g of 4-phenyl-1,2,4-triazolidine-3,5-dione, m.p. 202° to 203° C. (literature 203° C.) are obtained.

Starting material 4

60 g of hydrazodicarbonamide and 29 g of 1,6-diaminohexane in 100 ml of Sulfolan are stirred for 2 hours at 175° C. and 9 hours at 200° C. The precipitate which forms on cooling is suction-filtered and recyrstallised from water. 36 g (51% of the theoretical yield) of 1,6-hexane-diyl-4,4'-bis-1, 2,4-triazolidine-3,5-dione are obtained as colourless crystals, m.p. 215°–217° C.

| | | C | H | N |
|---|---|---|---|---|
| $C_{10}H_{16}N_6O_4$ | Calc.: | 42.25 | 5.67 | 29.51 |
| (284.3) | Found: | 42.5 | 5.7 | 29.2 |

Starting material 5

102 g of butane-1,4-diol-bis-(3-aminopropylether) and 120 g of hydrazodicarbonamide are stirred in 300 ml of N-methylpyrrolidone for one hour at 150° C., 2 hours at 175° C. and 5 hours at 200° C. The precipitate which forms on cooling is suction-filtered and boiled with 200 ml of acetonitrile. A residue of 142 g (76% of the theoretical yield) of 1,4-butanediol-bis-[3-(3,5-dioxo-1,2,4-triazolidin-4-yl)-propyl ether] is obtained as colourless crystals m.p. 152°–154° C.

| | | C | H | N |
|---|---|---|---|---|
| $C_{14}H_{24}N_6O_6$ | Calc.: | 45.15% | 6.50% | 22.57% |
| (372.4) | Found: | 45.2% | 6.6% | 22.6% |

IR (KBr): 1768, 1674 cm$^{-1}$ (C=O).

Starting material 6

111.5 g of semicarbazide hydrochloride are dissolved in 400 ml of water and neutralised with sodium carbonate. 57 g of methyl isocyanate dissolved in 300 ml of dioxane are then added dropwise within one hour with vigorous stirring at room temperature. Stirring is continued for a further 2 hours at room temperature and the precipitate formed is then separated by suction-filtration. The precipitate is suspended in 1 l of N-methylpyrrolidone and pyrrolised for 10 hours at 200° C. and 300 mbar. The solvent is subsequently distilled off under vacuum and the residue is recrystallised from ethanol. 96 g (83% of the theoretical yield) of 4-methyl-1,2,4- triazolidine-3,5-dione are obtained as colourless crystals, m.p. 230°–232° C. (Lit. 232°–233° C.).

Starting material 7

101 g of 1,2,4-triazolidine-3,5-dione and 57 g of 1,4-diaminocyclohexane in 500 ml of N-methylpyrrolidone are heated to 175° C. for 4 hours and to 200° C. for 30 hours with stirring. A precipitate crystallises on cooling. This is suction-filtered, washed with ethanol and dried. 110 g (78% of the theoretical yield) of 1,4-cyclohexanediyl-bis-(1,2,4-triazolidine-3,5-dion-4-yl) are obtained as colourless crystals, m.p. 300° C.

|  |  | C | H | N |
|---|---|---|---|---|
| $C_{10}H_{14}N_6O_4$ (282.2) | Calc.: | 42.56% | 4.96% | 29.75% |
|  | Found: | 42.7% | 5.1% | 29.1% |

MS (m/e): mol peak 282.

Starting material 8

100 g of 1,12-diaminododecane and 120 g of hydrazodicarbonamide in 300 ml of N-methylpyrrolidone are stirred for 1 hour at 175° C. and 4 hours at 200° C. The precipitate which forms on cooling is suction-filtered and boiled with 300 ml of acetonitrile. 156 g (85% of the theoretical yield) of 1,2-dodecane-4,4'-bis-(1,2,4-triazolidine-3,5-dione) are obtained as colourless crystals, m.p. 172°–175° C.

|  |  | C | H | N |
|---|---|---|---|---|
| $C_{16}H_{28}N_6O_4$ (368.5) | Calc.: | 52.16% | 7.66% | 22.81% |
|  | Found: | 52.2% | 7.7% | 22.6% |

MS (m/e): Mol peak 368.

EXAMPLE 1

2000 g of epichlorohydrin, 228 g of 1,2-ethandiyl-4,4'-bis-(1,2,4-triazolidine-3,5-dione) (starting material 1), 2 g of triethylamine and 200 ml of water are stirred under reflux conditions for 3.5 hours. The water is then removed by azeotropic distillation on a water separator. 170 g of sodium hydroxide in the form of 45% aqueous solution are addded dropwise to the reaction mixture at 40° C., to 45° C. under reduced pressure, and water is at the same time removed by azeotropic distillation on the water separator. Stirring is then continued at 40° to 45° C. until all the water has been removed. The sodium chloride formed is removed by suction-filtration and washed twice, each time with 200 g of epichlorohydrin. The combined epichlorohydrin solutions are extracted by shaking with 200 ml of water. After dehydration of the organic phase over sodium sulphate, the solvent is removed under vacuum and the residue is finally dried to constant weight at 60° C. and 0.3 mbar. 421 g of a pale yellow, highly viscous resin having an epoxide value of 0.82 and a chlorine content of 1.35% total chlorine are obtained.

EXAMPLE 2

37.8 g of 4,4'-bis-(1,2,4-triazolidine-3,5-dion-4-yl)-dicyclohexylmethane (starting material 2), 0.1 g of triethylamine and 300 g of epichlorohydrin are stirred under reflux for 5 hours. 16.5 g of pulverulent sodium hydroxide are added in small portions over a period of 2 hours to the solution cooled to 30° C., and stirring is continued for a further 2 hours at 30° C. in order to complete the reaction. The sodium chloride formed is separated by filtration and washed twice with 30 g portions of epichlorohydrin. The combined epichlorohydrin solutions are shaken with 50 ml of water. After dehydration of the organic phase over sodium sulphate, the solvent is removed under vacuum and the residue is finally dried to constant weight at 60° C. and 0.3 mbar. 52.1 g of a pale yellow, highly viscous oil having an epoxide value of 0.59 and a chlorine content of 2.1% total chlorine are obtained.

EXAMPLE 3

70.8 g of 4-phenyl-1,2,4-triazolidine-3,5-dione (starting material 3), 1 g of tetraethylammonium chloride and 500 g of epichlorohydrin are stirred for 5 hours at 80° C. After cooling of the reaction mixture to 40° C., 85 g of 40% sodium hydroxide solution are added dropwise within 2 hours. The water introduced into the reaction mixture and the water liberated in the reaction is removed from the reaction mixture over a water separator at reduced pressure. To complete the reaction, stirring is continued for one hour at 40° C. under azeotropic reflux. The sodium chloride obtained is separated by filtration and washed with 100 g of epichlorohydrin. The combined epichlorohydrin solutions are washed twice with 30 ml water and dehydrated over sodium sulphate. The epichlorohydrin is then distilled off under vacuum. The residue dried to constant weight at 70° C. and 0.2 mbar, weighs 107 g. The residue has an epoxide value of 0.66 and a chlorine content of 1.3% total chlorine.

EXAMPLE 4

56.8 g of 1,6-hexanediyl-4,4'-bis-(1,2,4-triazolidine-3,5-dione) (starting material 4), 0.5 g of thioglycol and 1.2 kg of epichlorohydrin are stirred for 7 hours at 100° C. After cooling of the reaction mixture, 46 g of potassium hydroxide are added dropwise as a 25% aqueous solution at 50° C. within 1.5 hours. The water introduced and formed in the reaction is removed from the reaction mixture over a water separator under reduced pressure. Stirring is continued for a further 2 hours at 50° C. under azeotropic reflux in order to complete the reaction. The potassium chloride formed is removed by washing with water. The epichlorohydrin solution is then dehydrated over sodium sulphate and concentrated by evaporation under vacuum. After drying to constant weight at 60° C. and 0.25 mbar, 95 g of a viscous, yellowish epoxide resin having an epoxide value of 0.73 and a chlorine content of 1.6% total chlorine are obtained.

EXAMPLE 5

55.8 g of 1,4-butane-bis-oxypropyl-3-diyl-(1,2,4-triazolidine-3,5-dion-4-yl) (starting material 5), 0.2 g of triethylamine and 1.2 kg of epichlorohydrin are stirred for 10 hours at 80° C. After cooling of the reaction mixture, 26 g of pulverulent sodium hydroxide are added in portions over a period of 3 hours at 30° C. The water of reaction is distilled off azeotropically with epichlorohydrin. The sodium chloride is removed by filtration and the remaining epichlorohydrin is distilled off under vacuum. After drying to constant weight at 70° C. and 0.4 mbar, a yellowish oil having an epoxide value of 0.61 and a chlorine content of 0.7% total chlorine is obtained.

EXAMPLE 6

(a) 115 g of 4-methyl-1,2,4-triazolidine-3,5-dione (starting material 6), 1 g of triethylamine and 750 g of epichlorohydrin are stirred under reflux for 4 hours. After cooling, 82 g of sodium hydroxide dissolved in 100 g of watter are added dropwise in the course of 4 hours at 35° C. and the water is removed from the reaction flask over a water separator under reduced pressure. Stirring is continued for 3 hours at 35° C. under azeotropic reflux at reduced pressure in order to complete the reaction, insoluble constituents are removed by suction filtration and the epoxide resin solution is freed from inorganic constituents by washing with water. After dehydration of the epoxide resin solution over Na$_2$SO$_4$, the solution is concentrated by evaporation from a rotary evaporator and the residue is dried to constant weight at 60° C. and 0.25 mbar. 190 g of a viscous, yellow epoxide resin having an epoxide value of 0.79 and a chlorine content of 1.1% total chlorine are obtained. This resin solidifies after it has been left to stand for 2 days. Trituration with ethanol results in substantially pure 1,2-bisglycidyl-4-methyl-1,2,4-triazolidine-3,5-dione, m.p. 115°–116° C. (from ethanol).

The IR and NMR spectra and elementary analysis confirm the assumed structure.

|  | C | H | N | Epoxide value |
|---|---|---|---|---|
| C$_9$H$_{13}$N$_3$O$_4$ | 47.57% | 5.77% | 18.50% | 0.88 |
| (227.2) | 47.6% | 5.7% | 18.6% | 0.88 |

(b) 21 g of triethylenetetramine are stirred into 100 g of a previously degasified crude epoxide resin having an epoxide value of 0.79 (from Example 6a) with cooling and the mixture is degasified. The mass is poured into a mould and hardened at room temperature.

A hard moulded product, light yellow in colour, is obtained after 12 days.

(c) 100 g of crystalline 1,2-bisglycidyl-4-methyl-triazolidine-3,5-dione and 135 g of hexahydrophthalic acid anhydride are melted separately, mixed at 120° C. and poured into a mould. After hardening for 10 hours at 120° C. and 2 hours at 160° C., samples having a Martens degree of 142° C. are obtained.

EXAMPLE 7

141 g of 1,4-cyclohexandiyl-bis-(1,2,4-triazolidine-3,5-dion-4-yl) (starting material 7), 0.5 ml of triethylamine and 1 kg of epichlorohydrin are stirred for 15 hours at 100° C. After cooling of the reaction mixture, 94 g of a 50% sodium hydroxide solution are added dropwise within 4 hours at 35° C. while the water is removed from the reaction vessel over a water separator at reduced pressure. Stirring is continued for a further 3 hours at 35° C. under azeotropic reflux at reduced pressure to complete the reaction. The epoxide resin solution is freed from insoluble constituents by suction filtration and from inorganic constituents by washing with water. After dehydration over sodium sulphate, the epoxide solution is concentrated by evaporation under vacuum, finally at 60° C. and 0.3 mbar. 187 g of a viscous epoxide resin having an epoxide value of 0.71 and a chlorine content of 1.1% total chlorine are obtained.

EXAMPLE 8

184 g of 1,12-dodecanediyl-4,4'-bis-(1,2,4-triazolidine-3,5-dione) (starting material 8), 0.5 ml of triethylamine and 1 kg of epichlorohydrin are stirred for 10 hours at 80° C. After cooling to 35° C. the reaction is continued as described in Example 7. 271 g of a viscous epoxide resin having an epoxide value of 0.52 and a chlorine content of 3.9% total chlorine are obtained.

EXAMPLE 9

200 g of the epoxide resin obtained according to Example 8 are dissolved in 500 g of methylene chloride. A quantity of sodium hydroxide equivalent to the chlorine content (+10% excess) is added dropwise in the form of 45% sodium hydroxide solution to this epoxide resin solution within 2 hours under reflux of the methylene chloride, and the water is removed from the reaction vessel over a water separator. After completion of the reaction, the reaction mixture is suction-filtered and the organic phase is washed with water and concentrated by evaporation, finally at 60° C./0.3 mbar. 188 g of a pale yellow epoxide resin having an epoxide value of 0.56 and a chlorine content of 0.4% total chlorine are obtained.

We claim:

1. A glycidyl-1,2,4-triazolidine-3,5-dione of the formula

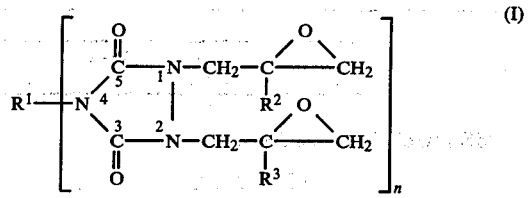

wherein R$^1$ is (a) C$_x$H$_{2x+1}$— wherein x = 1 to 18;
(b) —(CH$_2$)$_m$— wherein m = 2 to 12;

(c) $- \left[ \begin{array}{c} CH_2-CH-O \\ | \\ R^4 \end{array} \right]_p -CH_2-CH- \\ \phantom{xxxxxxxxxxxxxxxxxxxxx} | \\ \phantom{xxxxxxxxxxxxxxxxxxxxx} R^4$ wherein R$^4$ = H or CH$_3$ and p = 1–9;

(d) $- \left[ \begin{array}{c} CH_2-(CH_2)_q-N- \\ | \\ R^5 \end{array} \right]_r (CH_2)_q-CH_2-$ wherein R$^5$ = C$_1$–C$_4$-alkyl, q = 1–2 and r = 1–4;

(e) 

(f) 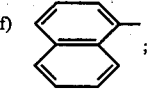

(g) 

(h) 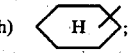

(i) 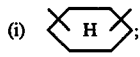

(j) 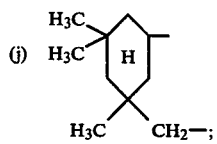

(k) 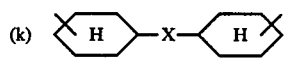

wherein X = alkylene having 1-4 C-atoms, O or —N(CH₃)—;

(l) 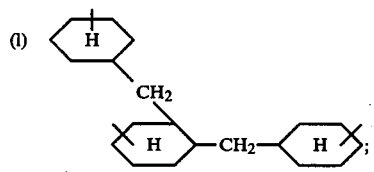

(m) 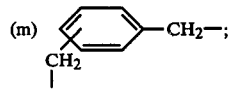

(n) 

(o) 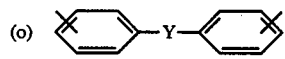

wherein Y = alkylene having 1-4 C-atoms, O or —N(CH₃)—;

(p) 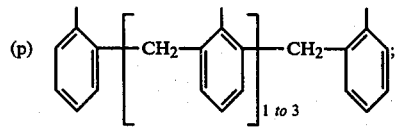

(q) C₄H₉—O—CH₂—CH₂—CH₂—;
(r) —(CH₂)₃—O—(CH₂)$_{\overline{2\,to\,4}}$O—(CH₂)₃—;

(s) 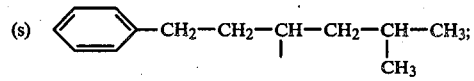

or one of said groups substituted by a member selected from the group consisting of alkoxycarbonyl having 1 to 4 carbon atoms in the alkoxy moiety, CN, NO₂, alkylmercapto having 1 to 4 carbon atoms, dialkylamino having 1 to 6 carbon atoms in each alkyl moiety and halogen;

R² and R³, which may be the same or different, are each hydrogen or methyl and n is a number from 1 to 5.

2. A glydicyl-1,2,4-triazolidine-3,5-dione of claim 1 wherein R² and R³ are each hydrogen.

3. A glycidyl-1,2,4-triazolidine-3,5-dione of claim 1 whose epoxide value is from 0.2 to 0.91.

4. A process for the preparation of a 1,2,4-glycidyl-triazolidine-3,5-dione according to claim 1 characterised in that a 1,2,4-triazolidine-3,5-dione corresponding to formula

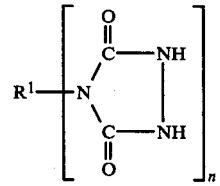

wherein R¹ and n are as defined in claim 1 for formula I, is reacted with an excess of epihalohydrin or β-methylhalohydrin to form the corresponding poly-(halohydrin) of the 1,2,4-triazolidine-3,5-diones of the formula (V) and the resulting poly-halohydrin is then converted into 1,2,4-glycidyl-triazolidine-3,5-dione of formula (I) by reaction with a hydrogen-halide-liberating agent.

5. A process according to claim 4, wherein the epihalohydrin used is epichlorohydrin.

6. A process according to claim 4, wherein from 1.2 to 20 mol of the epihalohydrin are used per NH group of the 1,2,4-triazolidine-3,5-dione.

7. A process according to claim 6, wherein from 3 to 10 mol of epihalohydrin are used per NH group.

8. A process according to claim 4, wherein the reaction between the 1,2,4-triazolidion-3,5-dione and the epihalohydrin is effected at 20° C. to 200° C.

* * * * *